(12) United States Patent
Rolli

(10) Patent No.: US 11,039,580 B2
(45) Date of Patent: Jun. 22, 2021

(54) AGROINDUSTRIAL PROCESS WITH MINIMAL ENVIRONMENTAL IMPACT

(71) Applicant: INDUSTRIE ROLLI ALIMENTARI S.P.A., Roseto degli Abruzzi (IT)

(72) Inventor: Gian Paolo Rolli, Frazione San Michele di Tiorre (IT)

(73) Assignee: INDUSTRIE ROLLI ALIMENT ARI S.P.A., Roseto Degli Abruzzi (IT)

( * ) Notice: Subject to any disclaimer, the term of this patent is extended or adjusted under 35 U.S.C. 154(b) by 569 days.

(21) Appl. No.: 15/759,449

(22) PCT Filed: Sep. 11, 2015

(86) PCT No.: PCT/IT2015/000220
§ 371 (c)(1),
(2) Date: Mar. 12, 2018

(87) PCT Pub. No.: WO2017/042841
PCT Pub. Date: Mar. 16, 2017

(65) Prior Publication Data
US 2018/0255716 A1 Sep. 13, 2018

(51) Int. Cl.
| | |
|---|---|
| *A01G 18/70* | (2018.01) |
| *A01G 22/00* | (2018.01) |
| *C05F 5/00* | (2006.01) |
| *C05F 7/00* | (2006.01) |
| *C12P 5/02* | (2006.01) |
| *C02F 11/04* | (2006.01) |
| *C05F 17/50* | (2020.01) |
| *C02F 3/28* | (2006.01) |
| *C02F 103/32* | (2006.01) |

(52) U.S. Cl.
CPC .......... *A01G 18/70* (2018.02); *A01G 22/00* (2018.02); *C02F 3/2893* (2013.01); *C02F 11/04* (2013.01); *C05F 5/008* (2013.01); *C05F 7/00* (2013.01); *C05F 17/50* (2020.01); *C12P 5/023* (2013.01); *C02F 2103/32* (2013.01); *Y02A 40/20* (2018.01); *Y02E 50/30* (2013.01); *Y02P 20/145* (2015.11); *Y02W 30/40* (2015.05)

(58) Field of Classification Search
None
See application file for complete search history.

(56) References Cited

U.S. PATENT DOCUMENTS

| | | | |
|---|---|---|---|
| 4,386,159 A | 5/1983 | Kanai | |
| 2002/0056302 A1* | 5/2002 | Tschudi | C05F 9/00 71/24 |
| 2006/0006111 A1 | 1/2006 | Holm et al. | |
| 2010/0173354 A1* | 7/2010 | Schwarz | C12M 45/03 435/41 |
| 2012/0118035 A1 | 5/2012 | Zhao et al. | |
| 2012/0231494 A1* | 9/2012 | Li | C12M 45/02 435/41 |
| 2012/0258522 A1* | 10/2012 | Eggersmann | C05F 17/50 435/267 |
| 2014/0273141 A1* | 9/2014 | Atwood | C10G 2/50 435/167 |
| 2015/0060356 A1* | 3/2015 | Barry | C05F 17/90 210/603 |

FOREIGN PATENT DOCUMENTS

| | | |
|---|---|---|
| CN | 101350096 A | 1/2009 |
| CN | 103396857 A | 11/2013 |
| CN | 103945687 A | 7/2014 |
| DE | 102010004543 A1 | 7/2011 |
| EP | 1914205 A1 | 4/2008 |
| JP | S53103853 A | 9/1978 |
| JP | 2002215717 A | 8/2002 |
| JP | 2003009663 A | 1/2003 |
| JP | 2003023887 A | 1/2003 |
| JP | 2003269252 A | 9/2003 |
| JP | 2004107144 A | 4/2004 |
| JP | 2004283133 A | 10/2004 |
| JP | 2005046116 A | 2/2005 |
| JP | 2006280252 A | 10/2006 |
| JP | 3136378 U | 10/2007 |
| JP | 2008253875 A | 10/2008 |
| JP | 2011121042 A | 6/2011 |
| JP | 2012025659 A | 2/2012 |
| JP | 2015501157 A | 1/2015 |

OTHER PUBLICATIONS

JP Office Action dated Jun. 4, 2019 re: Application No. 2018-533288, pp. 1-9, citing: JP 2005-046116 A, JP 2003-009663 A, JP 2006-280252 A, JP 003136378 U, JP S53-103853 A, JP 2004-107144 A, JP 2011-121042 A, US 2006/0006111 A, US 2012/0118035 A, JP 2008-253875 A, JP 2004-283133 A, JP 2002-215717 A, JP 2003-023887 A and JP 2003-269252 A.
EP Examination Report dated Apr. 29, 2020 re: Application No. 15 800 986.0—1106, pp. 1-6.
H. Boullagui et al. "Improvement of fruit and vegetable waste anaerobic digestion performance and stability with co-substrates addition", Journal of Evironment Management, Apr. 1, 2009 vol. 90, No. 5, pp. 1844-1849 XP026002590.

(Continued)

*Primary Examiner* — Wayne A Langel
(74) *Attorney, Agent, or Firm* — Cantor Colburn LLP

(57) ABSTRACT

An agro-industrial process with minimal environmental impact, of the type having a step of cultivating vegetable and/or mushroom products, includes a step of harvesting the products, at least one step of thermo-mechanical treatment of the products in order to obtain intermediate products, and a step of packaging of a final stage of the intermediate products.
The thermo-mechanical treatment step provides for a mechanical process of removing the unnecessary parts from the products so as to define waste. The waste, constituted exclusively by vegetable substances, is separated from the intermediate products, intended for the subsequent treatment and packaging steps, and sent into a biogas production unit. The digestate, constituted by the waste of the biogas production unit, is used as a fertilizer on the respective cultivation soil in a new step of cultivation of vegetable products.

7 Claims, No Drawings

(56) References Cited

OTHER PUBLICATIONS

International Search Report dated Apr. 28, 2016 re: Application No. PCT/IT2015/000220; pp. 1-6; citing: US 2006/006111 A1, DE 10 2010 004543 A1, H. Bouallagui et al. "Improvement of fruit . . . ", US 4 386 159 A and EP 1 914 205 A1.
Written Opinion dated Apr. 28, 2016 re: Application No. PCT/IT2015/000220; pp. 1-8; citing: US 2006/006111 A1, DE 10 2010 004543 A1, H. Bouallagui et al. "Improvement of fruit . . . ", US 4 386 159 A and EP 1 914 205 A1.

* cited by examiner

US 11,039,580 B2

AGROINDUSTRIAL PROCESS WITH MINIMAL ENVIRONMENTAL IMPACT

TECHNICAL FIELD

The present disclosure relates to an agro-industrial process with minimal environmental impact, in particular to a process that allows to cultivate and process industrially vegetables and mushrooms, reducing environmental impact.

BACKGROUND

Agro-industrial processes usually provide for a series of steps of agricultural nature (more specifically agronomic nature) within which, once the soil suitable for the cultivation has been identified, it is possible to proceed with its preparation, fertilization, seeding, distribution of any pesticides and harvesting of the vegetable and/or mushroom thus cultivated.

The vegetable and/or mushroom thus cultivated can then be transferred to an industrial unit, within which it will be subjected to processes suitable to convert it into a specific finished product.

Such processes provide for the elimination of waste parts (which are not edible or are of limited interest or are not compatible with the specific characteristics of the finished product to be provided), any washing, any thermal treatments (such as cooking, even only partial, deep freezing and the like) and packaging.

It is evident that such activities have a considerable environmental impact in relation to the energy consumption of the machines that process the vegetables and/or mushrooms, and it is equally evident that the waste parts must be appropriately separated for their disposal.

SUMMARY

The aim of the present disclosure is to solve the problems described above, by devising an agro-industrial process with minimal environmental impact that is suitable to minimize industrial waste.

Within this aim, the disclosure provides an agro-industrial process with minimal environmental impact in order to increase the value of the vegetable and/or mushroom waste.

The disclosure also provides an agro-industrial process with minimal environmental impact that is suitable to obtain an optimum energy balance.

The present disclosure further provides an agro-industrial process with minimal environmental impact that has low costs, is relatively simple to provide in practice and is safe in application.

This aim, as well as these and other advantages that will become better apparent hereinafter, are achieved by providing an agro-industrial process with minimal environmental impact, of the type comprising a step of cultivating vegetable and/or mushroom products, a step of harvesting said products, at least one step of thermo-mechanical treatment of said products in order to obtain intermediate products, and a step of packaging of a final stage of said intermediate products, wherein said thermo-mechanical treatment step provides for a mechanical process of removing the unnecessary parts from said products so as to define waste;

said waste, constituted exclusively by vegetable substances, is separated from the intermediate products, intended for the subsequent treatment and packaging steps, and sent into a biogas production unit; and the digestate, constituted by the waste of said biogas production unit that provides an anaerobic digestion that includes the breakdown, by microorganisms, of complex organic substances, such as lipids, proteins, glucids and of the recombination of the carbon and hydrogen contained therein to form methane and carbon dioxide, is used as a fertilizer on the respective cultivation soil in a new step of cultivation of vegetable products.

DETAILED DESCRIPTION

Further characteristics and advantages of the disclosure will become better apparent from the description of a preferred but not exclusive embodiment of the agro-industrial process with minimal environmental impact according to the disclosure.

The agro-industrial process with minimal environmental impact according to the disclosure is part of a production context of the type that comprises a step of cultivating vegetable and/or mushroom products, a step of harvesting the products, at least one step of thermo-mechanical treatment of the products, in order to obtain intermediate products, and a step of packaging a final stage of the intermediate products.

According to the disclosure, therefore, it is necessary to provide, in the industrial facility, at least one storage area for the vegetables that arrive from the cultivation field: in particular, the vegetables are harvested in cultivation fields located preferably at a substantially short distance from the building in which the facility is located, in order to minimize the time that elapses between harvesting and processing.

The facility further comprises at least one station for washing the vegetables that has the purpose of eliminating any residues of soil or other substances and materials that may have accumulated during harvesting; there is also at least one station for the mechanical treatment of the vegetables: the expression "mechanical treatment" is understood to reference the cutting (or generally the removal) of any parts of low or no interest, any extraction of the edible part of the vegetables from pods, peels and the like, and more generally all the activities that provide for direct mechanical intervention on the vegetable.

The presence of at least one station for the thermal treatment of said vegetables is also necessary: these vegetables can be subject to partial or total cooking by means of any one of the processes of the known type (by using thermal ovens, cooking griddles, cookers, flying machines and the like) and to a deep freezing within specific deep-freezing units.

The intermediate product subjected to the thermal treatment can then be sent to at least one respective packaging station, in which it can be inserted in the respective package.

Packaging can comprise a simple placement in a container; although this is not a priority interest of the present disclosure, the adoption of packaging units that operate in vacuum and/or in a modified atmosphere, in order to facilitate a longer life of the packaged product (with particular reference to a product packaged in an aseptic atmosphere and environment, usually therefore not deep frozen), is not excluded.

In the process according to the disclosure, the step of thermo-mechanical treatment provides, as described earlier, at least one mechanical process for removing the unnecessary parts from the products so as to form a waste (the waste parts have been partially listed earlier by way of nonlimiting example).

The waste thus obtained is separated from the intermediate products, which are intended for the subsequent processes that will lead to the provision of specific packaged foods and sent to a biogas production unit.

The biogas production unit comprises a fermentation tank, a manifold for collecting the gaseous substances generated as a consequence of fermentation, and a cogenerator.

The cogenerator is constituted by an internal combustion engine (which burns the combustible fraction of the produced biogas) and by an electromechanical generator: the heat energy that derives from the combustion is further collected and conveyed toward specific user units.

It is specified that in many cases the fermentation tank ensures a higher biochemical conversion efficiency if it is kept at specific temperatures: for this reason, the use of a predefined fraction of the heat energy to heat the fermentation tank is not excluded.

The biogas production unit provides an anaerobic digestion that includes the breakdown, by microorganisms, of complex organic substances, such as lipids, proteins, glucids, and of the recombination of the carbon and hydrogen contained therein in order to form methane and carbon dioxide.

As a consequence of this biochemical process, processing waste is identified which will constitute the so-called digestate (substances that have already undergone the biochemical process and therefore have reached a predefined stability level).

According to the process, the digestate is used as fertilizer on the respective cultivation soil in a new step of cultivation of vegetable products.

In practice, the digestate can be at least partially distributed on the fields intended for specific future cultivations, thus defining an iteration of the process according to the disclosure.

In this manner, it is pointed out that the process according to the disclosure is particularly virtuous, since it allows to generate a packaged food, constituted predominantly by vegetables and/or mushrooms, a predefined amount of energy (in the form of heat energy and electric energy obtained with the combustion of the combustible component of the biogas) and a predefined quantity of agricultural amendment and/or fertilizer. The process according to the disclosure therefore allows to minimize the environmental impact with respect to the impact normally generated by an agro-industrial process of a known type.

It is deemed useful to specify that the biogas production unit comprises a fermentation tank that is intended specifically to accommodate specific processing waste of agricultural origin and purification sludge.

The processing waste of agricultural origin is constituted in particular by the waste of the products subjected to the mechanical treatments in order to obtain the intermediate products; the purification sludge is generated during the step of treatment of the water used in the industrial transformation process in a treatment system that is present at the same site.

The treatment sludge comprises a liquid fraction (which constitutes the majority thereof) and a solid fraction.

According to a particular constructive solution of unquestionable interest in practice and in application, the fermentation tank of the biogas production unit accommodates a mixture that is constituted by sludge in a percentage comprised between 60% and 80% (preferably around 70%), waste of the products being processed in a percentage comprised between 5% and 10% (preferably around 7%), corn and triticale in a percentage comprised between 20% and 30% (preferably around 23%).

The sludge can be also integrated by the liquid fraction of a digestate related to a previous fermentation cycle.

The corn is preferably present in the form of shredded material and is selected among the varieties that are best suited to be used for the purpose.

The term "triticale" is understood to reference an artificial hybrid between rye and durum wheat or other varieties of the *Triticum* genus. The addition of silage to the above is not excluded, silage being the product of a forage preservation method (ensilage) provided by acidification of the vegetable mass by anaerobic microorganisms in order to prevent altering and potentially toxic microorganisms from proliferating within the vegetable mass, producing its consumption (loss of nutritional value) and the generation of unhealthy substances in general.

It should be pointed out that according to the disclosure the digestate comprises a liquid phase and a solid phase.

The liquid phase comprises ammonia nitrogen, $N\text{—}NH_4$, phosphoric acid, $H_3PO_4$, phosphorus ions and salts, potassium ions and salts, calcium ions and salts, magnesium ions and salts, sulfates and trace elements, while the solid phase comprises ammonia nitrogen as a main element that has an agricultural amendment function.

It should also be specified that the digestate is constituted, for a percentage comprised between 8% and 15%, by the solid phase and, for a percentage comprised between 85% and 92%, by the liquid phase: more specifically, the digestate comprises by way of indication about 10% constituted by the solid phase, which can be used effectively as an amendment in cultivated soils, by way of example about 90% constituted by the liquid phase that is partially (approximately for 40%) reintroduced in the fermentation tank of the biogas production unit and for the remaining part (by way of example 50%) is treated by means of a centrifuge or a belt press in order to be converted into a so-called clarified fraction that gathers in the oxidation tank of the purification plant.

According to a particular embodiment of the process according to the disclosure, part of the liquid phase by which the digestate is constituted is returned directly to the fermentation tank of the biogas production unit in order to take part again in the biochemical transformation, mixed with the purification sludge.

According to a further embodiment of the process according to the disclosure, the liquid phase can be stored or distributed on the fields as fertilizer, optionally after submitting it to at least one process selected among stabilization, denitrification and the like (a process that might be useful to improve its role as amendment for specific crops and/or for soil with specific pedologic and/or chemical-physical characteristics).

With particular reference to an embodiment of the disclosure that is particularly efficient and suitable for an exploitation of the digestate that is careful and respectful of the environment, the solid phase is stored (for future use directly and/or mixed with other substances) or spread on fields as fertilizer.

According to a particular embodiment of the present disclosure, aimed at minimizing the environmental impact of the crop and the content of pesticides released into the environment, the step of cultivation of vegetable products and/or mushrooms includes the following steps:

performing a preventive chemical, physical and pedologic analysis of the soils intended for the crop, in order to identify at least partially its composition, humidity and temperature and to verify the absence of pathogens, infesting organisms and pollutants;

selecting, among natural seeds and mycelia, not genetically modified, the ones that are most suitable for the previously identified soil parameters;

performing iterated periodic checks of the cultivated vegetables, mushrooms that grow after seeding, in order to detect pathologies and/or infestations thereof;

performing at least one plant protection treatment by using active ingredients selected among insecticides, herbicides, acaricides, limacides and fungicides;

close to the harvesting period, performing iterated periodic spot checks of the cultivated vegetables, mushrooms, in order to measure the residual concentration of active ingredients for plant protection; and upon detections of the residual concentration of active ingredients for plant protection below a predefined threshold, harvesting the cultivated vegetables, mushrooms.

It is also necessary to point out that the biogas generation unit comprises a collection manifold for the gaseous substances generated as a consequence of fermentation and a selection device for dividing said gaseous substances.

Such gaseous substances comprise 50÷70% methane, carbon dioxide, water vapor, hydrogen sulfide and other gaseous substances in small quantities.

It is specified that the biogas produced by adopting the process according to the disclosure has a heat value on the order of 23,000 kJ/Nm$^3$.

A biogas production unit suitable to implement a process according to the disclosure comprises an anaerobic digestion system for producing biogas by using the vegetable waste and the sludge of the purification plant of the facility in which the processing of the vegetables and/or mushrooms takes place.

A unit suitable for a facility with dimensions and characteristics that are very widespread in the agroalimentary sector can have a nominal power of 1 MW.

An apparatus that produces and utilizes the biogas can be shown schematically as being constituted by two main parts:
 the fermentation tank, in which the anaerobic digestion process occurs and in which methane is released;
 the cogenerator, which uses the generated methane to produce electric power and steam.

A biogas production unit uses biomasses, the term understood to reference all substances of biological origin in non-fossil form: materials and residues originating from agriculture and forests, secondary products and waste of the agroalimentary industry, zootechnical wastewater, organic fraction of municipal waste, purification sludge, algae and many vegetable species used for the purification of organic sludge.

The process according to the disclosure provides for the exclusive use of processing waste of agricultural origin and purification sludge that arrive from the purification system, which processes exclusively the wastewater generated by the process for the transformation of agricultural products.

Since the purification plant treats the wastewater used in the industrial transformation process, the presence in the corresponding sludge for example of residues of ingredients used in one of the recipes intended for production is not excluded.

The extent of such substances dissolved in water is in any case a minimal percentage and therefore even if they are introduced in the fermentation tank they have no effect on the process and are unable to modify the indicated percentages of the components.

Obviously, the percentage of methane within the biogas varies depending on the type of organic substance that is digested and on the process conditions.

At the end of the fermentation process, the main nutrient elements (nitrogen, phosphorus, potassium) already present in the raw material are preserved intact in the effluent, facilitating the mineralization of the organic nitrogen; in particular, the digestate is an excellent fertilizer, in which the nitrogen is in a form that can be assimilated directly by the plants.

Downstream of the digester, the digestate (i.e., the material treated in anaerobic digestion) can be separated mechanically, retaining a solid part (8-15%, preferably around 10%) and with a high fertilizing value, which can be further dried and composted, and a liquid part (85-92%) that is stabilized and ready for additional treatments (denitrification) or for reintroduction in the fermentation tank and/or temporary storage.

The use of digestates is an integration of an organic nature to the mineral nutrition of the cultivated plants and a contribution to maintaining the agronomic fertility of soils. Furthermore, their use instead of chemical fertilizers improves the environmental and energy balance and the cost saving can reach €100/ha.

A particular application of the process according to the disclosure entails that only the solid fraction of the digestate is used as amendment on the fields. The liquid fraction is instead reintroduced in the digester to improve/stabilize the anaerobic process.

In order to illustrate the context within which the process according to the disclosure lies, the steps of some examples of production flow that can be performed are listed.

Production of a natural intermediate product (frozen peas)
Feeding of fresh vegetable
Vibration, ventilation and stone removal (with generation of vegetable waste for the fermentation tank of the biogas unit)
Pod separation
Washing
Scorching
Cooling
Selection (with generation of vegetable waste for the fermentation tank of the biogas unit)
Deep freezing
Ventilation (with generation of vegetable waste for the fermentation tank of the biogas unit)
Screening with vibrating screen (to define the calibers)
Filling of packages and weight checking
Storage in a cell at −18° C.
Production of a grilled intermediate product (grilled eggplants)
Feeding of fresh vegetable
Washing/stone removal
Topping (with generation of vegetable cuttings for the fermentation tank of the biogas unit)
Cutting (with generation of vegetable cuttings for the fermentation tank of the biogas unit)
Vibration (with generation of vegetable waste for the fermentation tank of the biogas unit)
Selection (with generation of vegetable waste for the fermentation tank of the biogas unit)
Optional oiling
Grilling in an oven
Cooling
Deep freezing
Checking with metal detector
Filling of package and weight checking Storage in a cell at −18° C.

Advantageously, the present disclosure solves the problems described earlier, devising an agro-industrial process with minimal environmental impact suitable to minimize industrial waste.

The waste of agricultural products is in fact used to feed the biogas production unit, said biogas being subsequently used to feed a cogenerator that allows to have electric power and heat energy available.

Moreover, the digestate that exits from the biogas production unit can be used (both in its liquid fraction and in its solid fraction) as agricultural amendment and, more generally, as fertilizer.

Efficiently, the agro-industrial process with minimal environmental impact allows therefore to increase the value of the waste of vegetables and/or mushrooms, which otherwise would be, for the industry that deals with the process, a waste to be disposed of (in accordance with currently applicable statutory provisions on the matter).

Conveniently, the agro-industrial process according to the disclosure is suitable to obtain a better energy balance. The energy balance (consumed energy with respect to produced energy) is advantageous for anyone who performs the process according to the disclosure by way of the energy production that is provided by the cogenerator supplied by the internally produced biogas.

Positively, the agro-industrial process according to the disclosure, once started, is sustainable with low costs in a relatively simple manner and for these reasons is safe in application.

The fact that the digestate produced by means of the process according to the disclosure entails a lower environmental impact (with respect to other types of digestate that can be obtained from different plants that do not perform the process according to the disclosure) is particularly favorable: the digestate obtained by applying the process according to the disclosure in fact does not pollute, since it is obtained from the digestion of vegetable substances and is free from sludge contamination; this digestate has fewer odor generation problems with respect to digestate or manures of animal origin; the digestate obtained by applying the process according to the disclosure constitutes an organic amendment with a low nitrogen content, well below the legal limits (2%), which allows its use even in nitrate susceptible soil; the digestate obtained herein, furthermore, does not comprise PAH (polycyclic aromatic hydrocarbons) and can contain heavy metals (Cd, Hg, Pb, . . . ) in a quantity that is monitored and is in any case well below the legal limits.

The digestate obtained by way of the application of the process according to the disclosure comprises a dry residue at 105° C. on the order of 12%/23% (exemplifying experimental tests have indicated that a typical detectable value is 17.1%, of which 5.5% is constituted by organic carbon, 0.8% is constituted by nitrogen, and 93.7% is constituted by other elements).

The disclosure thus conceived is susceptible of numerous modifications and variations: all the details may further be replaced with other technically equivalent elements.

In the examples of embodiment shown, individual characteristics, given in relation to specific examples, may actually be interchanged with other different characteristics that exist in other examples of embodiment.

In practice, the materials used, as well as the dimensions, may be any according to requirements and to the state of the art.

The invention claimed is:

1. An agro-industrial process with minimal environmental impact having a step of cultivating vegetable and/or mushroom products, includes a step of harvesting said products, at least one step of thermo-mechanical treatment of said products in order to obtain intermediate products, and a step of packaging a final stage of said intermediate products, wherein
   said thermo-mechanical treatment step provides for a mechanical process of removing the unnecessary parts from said products so as to define waste;
   said waste, constituted exclusively by vegetable substances, is separated from the intermediate products, intended for the subsequent treatment and packaging steps, and sent into a biogas production unit; and
   the digestate, constituted by the waste of said biogas production unit that provides an anaerobic digestion that includes the breakdown, by microorganisms, of complex organic substances, such as lipids, proteins, glucids and of the recombination of the carbon and hydrogen contained therein to form methane and carbon dioxide, is used as a fertilizer on the respective cultivation soil in a new step of cultivation of vegetable products,
   wherein said biogas production unit comprises a fermentation tank that contains process waste of agricultural origin, comprising said waste of said products, and purification sludge generated by the purification plant inside the facility in which wastewater used in the transformation process is treated, said purification sludge comprising a predominant liquid fraction and a solid fraction,
   wherein said fermentation tank contains said purification sludge in a percentage comprised between 60% and 80%, said waste of said products in a percentage comprised between 5% and 10%, corn and triticale in a percentage comprised between 20% and 30%, and a liquid fraction of a corresponding digestate.

2. The agro-industrial process according to claim 1, wherein said digestate comprises a liquid phase and a solid phase, said liquid phase comprising ammonia nitrogen, $N-NH_4$, phosphoric acid, $H_3PO_4$, phosphor ions and salts, potassium ions and salts, calcium ions and salts, magnesium ions and salts, sulfates and trace elements, said solid phase comprising ammonia nitrogen.

3. The agro-industrial process according to claim 2, wherein said digestate is constituted by said solid phase for a percentage comprised between 8% and 15%, and by said liquid phase for a percentage comprised between 85% and 92%.

4. The agro-industrial process according to claim 2, wherein said liquid phase is returned, for a total quantity of 40/45%, directly to the fermentation tank of said biogas production unit.

5. The agro-industrial process according to claim 2, wherein said solid phase is stored or spread on the fields as fertilizer.

6. The agro-industrial process according to claim 1, wherein said step of cultivation of vegetable and/or mushroom products includes the following steps:
   performing a preventive chemical, physical and pedologic analysis of the soils intended for the crop, in order to identify at least partially the composition, humidity and temperature thereof and to check for the absence of pathogens, infesting organisms and pollutants;
   selecting, among natural seeds and mycelia, not genetically modified, the ones that are configured for the previously identified soil parameters;

performing iterated periodic checks of the cultivated vegetables and/or mushrooms, that grow after seeding, in order to detect pathologies and/or infestations thereof;

performing at least one plant protection treatment by using active ingredients selected among the group consisting of insecticides, herbicides, acaricides, limacides, and fungicides;

close to the harvesting period, performing iterated periodic spot checks of the cultivated vegetables and/or mushrooms, in order to measure the residual concentration of active ingredients for plant protection; and upon detections of the residual concentration of active ingredients for plant protection below a predefined threshold, harvesting the cultivated vegetables and/or mushrooms.

7. The agro-industrial process according to claim 1, wherein said biogas production unit comprises a collection manifold for the gaseous substances generated as a consequence of fermentation, which comprise 50÷70% methane, carbon dioxide, water vapor, hydrogen sulfide, and other gases, and a selection device for dividing said gaseous substances, said biogas having a heat value on the order of 23,000 $kJ/Nm^3$.

* * * * *